US00PP17311P2

(12) United States Plant Patent
Hansen

(10) Patent No.: US PP17,311 P2
(45) Date of Patent: Dec. 26, 2006

(54) ***HOSTA* PLANT NAMED 'MOURNING DOVE'**

(50) Latin Name: *Hosta hybrida*
Varietal Denomination: Mourning Dove

(75) Inventor: Hans Andrew Hansen, Waseca, MN (US)

(73) Assignee: Shady Oaks Nursery, LLC, Waseca, MN (US)

( * ) Notice: Subject to any disclaimer, the term of this patent is extended or adjusted under 35 U.S.C. 154(b) by 12 days.

(21) Appl. No.: 11/230,859

(22) Filed: Sep. 20, 2005

(51) Int. Cl.
*A01H 5/00* (2006.01)

(52) U.S. Cl. ..... Plt./353
(58) Field of Classification Search ..... Plt./353
See application file for complete search history.

(56) References Cited

PUBLICATIONS http://www.shadyoaks.com/GeneratedItems/Pages/Hosta6.html.*

* cited by examiner

*Primary Examiner*—Wendy Haas
(74) *Attorney, Agent, or Firm*—Penny J. Aguirre

(57) ABSTRACT

A new cultivar of *Hosta* named 'Mourning Dove', that is characterized by its unique variegated foliage of wedge-shaped leaves with blue-green centers and yellow-green margins comprising about one fourth of the leaf area. 'Mourning Dove' is a medium sized *Hosta* with a flat mounded plant habit that blooms in late summer with lavender flowers that arise on scapes held almost horizontal to the foliage.

1 Drawing Sheet

Botanical classification: *Hosta hybrida.*
Cultivar designation: 'Mourning Dove'.

BACKGROUND OF THE INVENTION

The present invention, *Hosta* 'Mourning Dove', relates to a new and distinct cultivar of *Hosta*, botanically known as a *Hosta hybrida*, hereinafter referred to as 'Mourning Dove'.

'Mourning Dove' was selected in 2002 and originated from a controlled cross, designated 98-164, made by the inventor in 1998 in Waseca, Minn. The pod parent was a streaked variegated form of *Hosta* 'Mikawa-no-yuki' (not patented) and the pollen parent was *Hosta* 'Blue Jay' (not patented). The pollen parent, 'Blue Jay', is non-variegated. 'Mourning Dove' also differs from 'Blue Jay' in having a better growth rate and in having longer, more wedge-shaped leaves.

Asexual reproduction of the new cultivar was first accomplished by the inventor by division in Waseca, Minn. in 2003. Asexual reproduction of the new cultivar by division and tissue culture has shown that the unique features of 'Mourning Dove' are stable and reproduced true to type in successive generations.

SUMMARY OF THE INVENTION

The following traits have been repeatedly observed in trials in Minnesota for a period of six years and represent the characteristics of the new cultivar. These attributes in combination distinguish 'Mourning Dove' as a new and unique cultivar of *Hosta.*

1. The foliage of 'Mourning Dove' is variegated with intense blue-green centers and yellow-green margins that comprise about one fourth of the leaf area.
2. The leaves of 'Mourning Dove' are wedged-shaped.

3. 'Mourning Dove' is a medium sized *Hosta* with a flat but mounded plant habit, reaching a height of about 30 cm (12 inches, exclusive of flower scapes) and a spread of about 78 cm (31 inches).
4. 'Mourning Dove' blooms in early August with lavender flowers that arise on scapes held almost horizontal to the foliage.

BRIEF DESCRIPTION OF THE DRAWING

The accompanying colored photograph illustrates the overall appearance and distinct characteristics of the new *Hosta* as grown outdoors in Waseca, Minn. for a period of six years. The photograph was taken in July and is represents the summer foliage of 'Mourning Dove'. The colors in the photograph are as close as possible with the photographic and printing technology utilized and combined with the color values cited in the detailed botanical description accurately describe the colors of the new *Hosta.*

DETAILED BOTANICAL DESCRIPTION OF THE PLANT

The following is a detailed description of six year-old plants of the new cultivar as grown outdoors in Waseca, Minn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Mourning Dove' is a cultivar of *Hosta hybrida.*

Parentage: Pod parent; streaked form of *Hosta* 'Mikawa-no-yuki' (not patented), pollen parent *Hosta* 'Blue Jay' (not patented).

General description:

*Blooming period.*—Typically August 1st to August 20th in Minnesota.

*Plant habit.*—Herbaceous perennial, clump-forming, flat mounded habit.

*Height and spread.*—Reaches about 30 cm (12 in) in height (excluding flower scapes) and about 78 cm (31 in) in width.

*Hardiness.*—U.S.D.A. Zones 3 to 8.

*Culture.*—Light to full shade, moist soils of moderate fertility.

*Diseases and pests.*—No susptibility or resistance to diseases or other pests has been observed for 'Mourning Dove'.

*Root description.*—Freely branched, fleshy.

*Propagation.*—*In vitro* propagation is the preferred method utilizing typical methods for *Hosta,* division is also possible.

*Root development.*—Rooted transplants from tissue culture fully develop in a 96-cell liner in about 6 to 8 weeks in a greenhouse with average temperatures of about 70° F.

*Growth rate.*—Moderate.

Foliage description:

*Leaf shape.*—Broadly lanceolate.

*Leaf division.*—Simple.

*Leaf base.*—Rounded.

*Leaf apex.*—Acuminate.

*Leaf venation.*—About 8 pairs of veins, campylodrome pattern, impressed on upper surface and raised on lower surface, color on upper surface 145A, color matches foliage coloration on lower surface.

*Leaf margins.*—Entire.

*Leaf attachment.*—Petiolate.

*Leaf arrangement.*—Basal, radiate spirally from base.

*Leaf surface.*—Glaucous on upper and lower surface in spring, glabrous on upper surface and glaucous on lower surface on summer foliage, lower surface on both spring and summer foliage is highly glaucous.

*Leaf substance.*—Average.

*Leaf orientation.*—Held nearly upright on petioles that are upright or up to about a 45° angle to center.

*Leaf variegation pattern.*—Margins comprise about one quarter of the leaf area and average about 1.2 cm in width, the centers are primarily lanceolate in shape, intermediate areas exists in an irregular pattern between the boundaries of the margins and centers on the summer foliage, they are not conspicuous. The variegation is more distinct on summer foliage.

*Leaf color.*—Spring foliage, upper surface; centers 137A (slightly darker) overlaid with glaucous coating, margins 138A overlaid with glaucous coating, lower surface; centers and margins 191A with coating of 191D. Summer foliage, upper surface; centers 137A (slightly darker), margins 151B TO 151D, intermediate areas 191A, lower surface; centers 137B with a glaucous coating of 189C, margins 144A with glaucous coating of 191B, intermediate area not distinct.

*Leaf size.*—Average of 19.7 cm in length, average of 9.5 cm in width.

*Leaf quantity.*—About 5 to 7 per shoot (eye).

*Petiole size.*—About 20 cm in length, average 0.5 mm in width.

*Petiole color.*—Inner surface 138A at margins to 138B in centers, outer surface 138A in margins, 193A in centers.

*Petiole surface.*—Glabrous, both surfaces.

*Petiole shape.*—Sulcate.

Flower scape description:

*Scape shape.*—Round, solid.

*Scape number.*—One per mature eye under normal growing conditions.

*Scape posture.*—Held almost horizontal.

*Scape size.*—About 40 to 50 cm in length, about 4 mm in width.

*Scape color.*—144B.

*Scape surface.*—Slightly glaucous.

*Leaf bracts.*—About 3, about 2.7 cm in length and 1 cm in width, papery, lanceolate in shape, 158C in color blushed and thin lines of N77C.

Flower description:

*Inflorescence type.*—Terminal racemes of single tubular-shaped flowers, clustered near terminus of scape.

*Lastingness of inflorescence.*—About 3 weeks from first opening bloom to fading of last opening bloom, individual blooms last about one day.

*Flower shape.*—Tubular.

*Flower number.*—About 25.

*Flower internode length.*—Up to about 1 cm, upper flowers are congested in cluster.

*Flower fragrance.*—None detected.

*Flower bud shape.*—Spathulate.

*Flower bud size.*—Up to about 3.5 cm in length and 1 cm in diameter.

*Flower bud color.*—Emerges 155B with lines of N77C, matures to 84D prior to opening.

*Flower size.*—Up to about 5 cm in length and about 1.5 cm in diameter.

*Flower color.*—Opens 84D, matures to 85B to 85C.

*Pedicels.*—About 4 mm in length and 2 mm in diameter, 84D in color.

*Perianth features.*—Comprised of 6 tepals, 3 interior and 3 exterior, fused in tube region and about one half of expanded region than overlapping towards apex.

*Tepal shape.*—Lanceolate.

*Tepal size.*—About 3.5 cm in length, about 5 mm in width.

*Tepal color.*—Outer and inner surface 84D with blush and fine lines of 85B.

*Tepal texture.*—Glabrous.

*Floral bracts.*—1 per flower, lanceolate in shape, papery, 158C in color blushed and thin lines of N77C, about 2.2 cm in length and 7 mm in width.

Reproductive organs:

*Gynoecium.*—1 Pistil. Style is about 4 cm in length, 1 mm in width and 150C in color. Stigma is 3-lobed, 150C in color and 0.75 mm in diameter. Ovary is superior, compound, composed of 3 locules, oblong in shape, 5 mm in length, 2 mm in width and 144C in color.

*Androecium.*—6 stamens, filament is 150C in color, about 4 cm in length, 0.7 mm in width, length about equal with perianth, anthers are 3.5 mm in length, 1 mm in width, attachment is versatile, 202A in color, dehiscence is longitudinal, pollen is abundant and 14A in color.

*Fruit*.—Capsule, 3-chambered, about 2.2 cm in length, 5 mm in width, 138A in color.

*Seeds*.—About 10 seeds per capsule, about 8 mm in length and 3 mm in width, 202A in color.

I claim:

1. A new and distinct cultivar of *Hosta* plant named 'Mourning Dove' as herein illustrated and described.

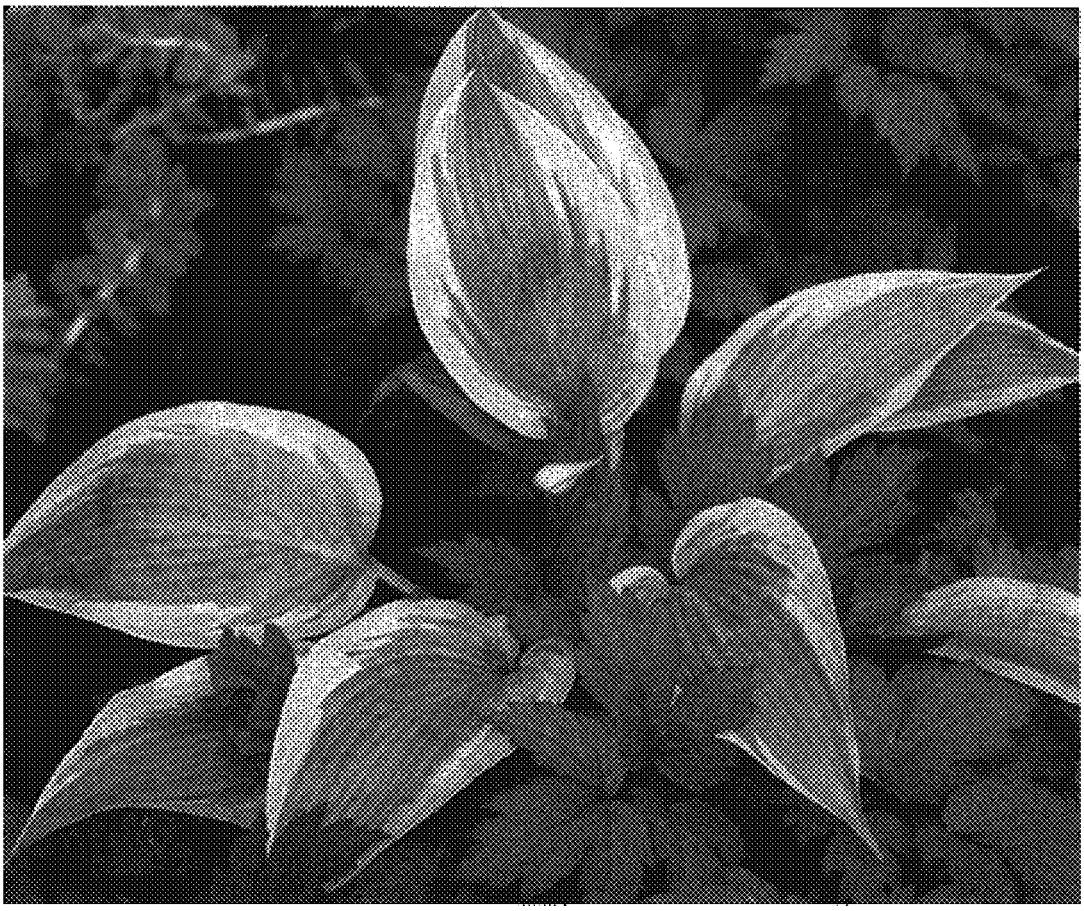

* * * * *